United States Patent [19]

Lamont

[11] Patent Number: 5,367,789
[45] Date of Patent: Nov. 29, 1994

[54] PROTECTIVE MEDICAL BOOT AND ORTHOTIC SPLINT

[75] Inventor: William D. Lamont, Shelby Township, Maccomb County, Mich.

[73] Assignee: LaMED, Inc., Shelby Township, Maccomb County, Mich.

[21] Appl. No.: 90,895

[22] Filed: Jul. 12, 1993

Related U.S. Application Data

[63] Continuation-in-part of Ser. No. 763,335, Sep. 20, 1991, Pat. No. 5,226,245.

[51] Int. Cl.$^5$ ............................ A43B 7/14; A43B 1/02; A61F 3/00
[52] U.S. Cl. ...................................... 36/9 R; 128/892; 602/28
[58] Field of Search ....................... 36/9 R, 93, 110, 89, 36/90; 128/882, 892; 602/24, 27, 28

[56] References Cited

U.S. PATENT DOCUMENTS

| | | |
|---|---|---|
| Re. 33,090 | 10/1989 | Berguer .................................. 36/9 R |
| 2,906,261 | 9/1959 | Craig ...................................... 602/24 |
| 3,511,233 | 5/1970 | Holy, Jr. ................................ 128/149 |
| 3,606,884 | 9/1971 | Peter ..................................... 128/892 |
| 3,814,088 | 6/1974 | Raymond .............................. 602/27 |
| 3,827,430 | 8/1974 | Fadden .................................. 602/28 |
| 4,076,022 | 2/1978 | Walker .................................. 128/149 |
| 4,197,845 | 4/1980 | Browning .............................. 128/149 |
| 4,454,871 | 6/1984 | Mann et al. ............................ 602/27 |
| 4,478,214 | 10/1984 | Lamont ................................. 128/149 |
| 4,520,803 | 6/1985 | Quest ..................................... 602/24 |
| 4,813,162 | 3/1989 | Harris .................................... 36/88 |
| 5,088,479 | 2/1992 | Detoro ................................... 602/27 |
| 5,143,058 | 9/1992 | Luber et al. .......................... 602/28 |
| 5,154,695 | 10/1992 | Farris et al. .......................... 128/892 |
| 5,224,925 | 7/1993 | Varn ...................................... 602/28 |
| 5,226,245 | 7/1993 | Lamont ................................. 36/9 R |

Primary Examiner—Steven N. Meyers
Attorney, Agent, or Firm—Charles W. Chandler

[57] ABSTRACT

A soft medical boot having an articulated splint bar for adjusting the angle of the foot of a patient disposed in a supine position.

3 Claims, 9 Drawing Sheets

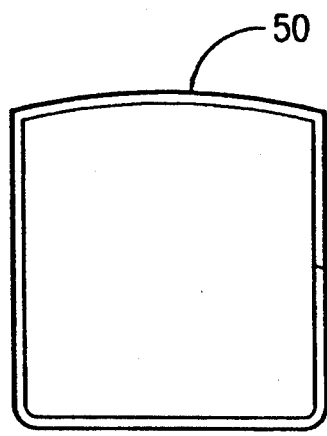
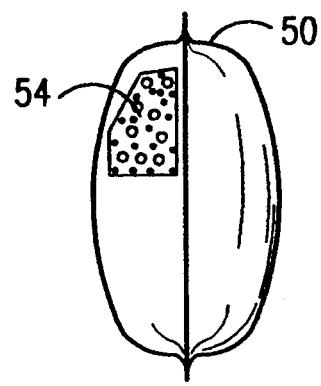
FIG. 4    FIG. 5
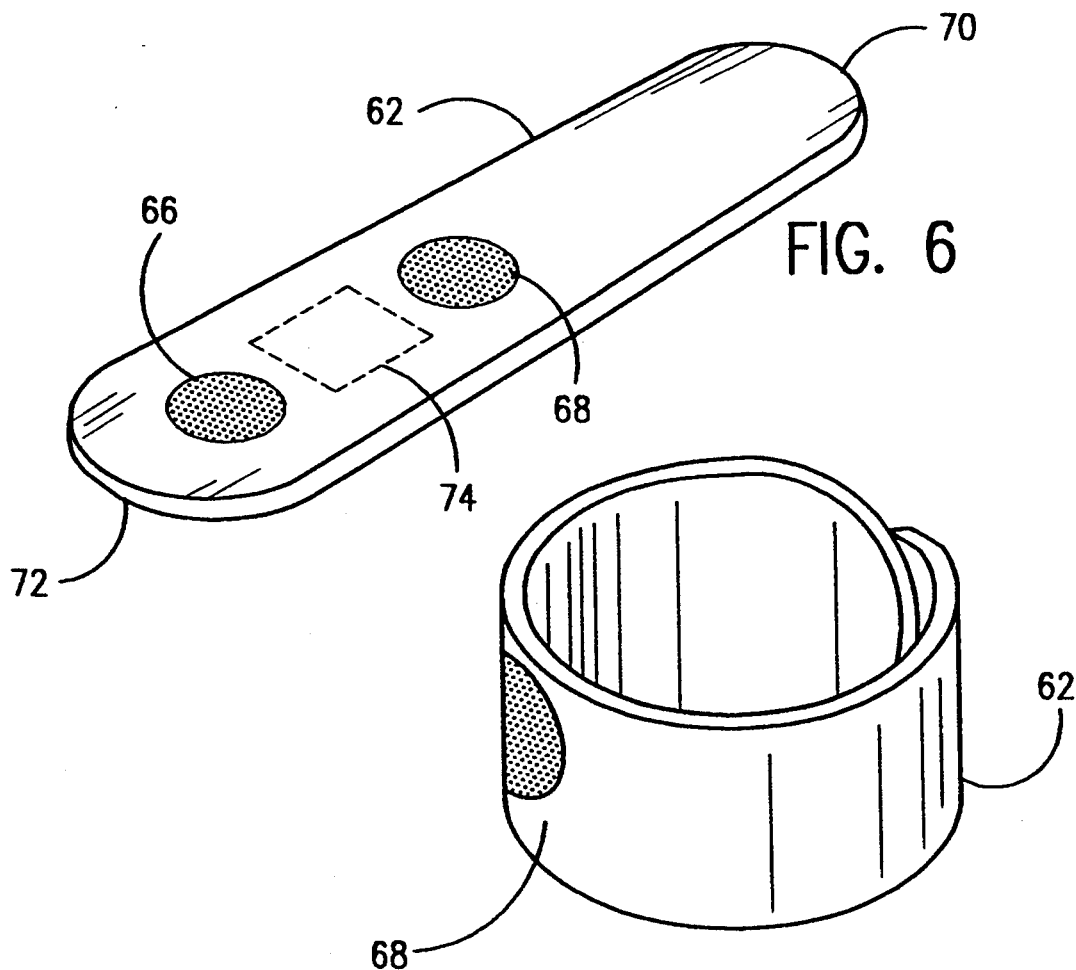
FIG. 6
FIG. 7

PROTECTIVE MEDICAL BOOT AND ORTHOTIC SPLINT

CROSS REFERENCE TO RELATED APPLICATION

This application is a continuation-in-part of my co-pending application Ser. No. 07/763,335 filed Sep. 20, 1991 for PROTECTIVE BOOT STRUCTURE and which is intended to be issued Jul. 13, 1993 with U.S. Pat. No. 5,226,245.

BACKGROUND OF THE INVENTION

This invention is related to a medical boot and a supporting splint for treating or avoiding decubitus ulcers, especially for patients with heel, toe and foot pressure ulcers.

Decubitus ulcers are pressure sores commonly found in patients of hospitals and other institutions. Such sores add considerably to patient nursing time and to the cost of medical care. Complications associated with pressure sores may be life-threatening. Many devices are known in the prior art, some of which are commercially-available, for treating or avoiding such sores, however, they are frequently unsatisfactory because they are not responsive to the underlying causes of the sores.

Pressure sores can develop over any bony prominence or area subjected to prolonged pressure, such as on the heel. A pressure gradient in the area of the sore is one of the causes of such sores. Blood vessels, muscles, subcutaneous fat and skin frequently are pressed between a bone and a sleeping surface. Pressure is transmitted from the body toward the bone. Soft tissue compressed between a bony prominence and a firm external surface is susceptible to tissue destruction. The external surface produces pressure, and the bone produces counter pressure. These opposing surfaces result in a pressure gradient involving the tissue between the external surface and the skeletal anatomy involved. The greatest tissue destruction is beneath the skin surface.

Another factor that contributes to the mechanical destruction of tissue is a shear effect, which mainly occurs in deep tissues. The tissue attached to the bone is pulled in one direction because of the body weight while the surface tissue sticks to the bed linen and remains stationary. The body skeleton actually slides inside the skin. A shearing force can occur when patients are dragged along the surface of the sheets during repositioning.

Friction is another factor that develops pressure sores. Two surfaces moving across one another create friction. Friction commonly occurs in patients who are unable to lift themselves sufficiently for repositioning. If a patient is pulled across the bed linen, the outer protective layer of skin may be rubbed away by abrasion. This mechanical wearing away of surface tissue increases the potential for deeper tissue damage. Patients who have appliances that rub against the skin are also at high risk for tissue damage by friction.

Other factors such as exposure to moisture can macerate the skin. Maceration contributes to pressure ulcers because the excessive moisture softens the connective tissue.

Many commercial devices are available on the market for avoiding or treating pressure sores. These include for example, "The Vascular Boot" available from Lunax Corporation of Bloomfield Hills, Mich.; the Jerome 0355 "Bed Boot" available from Orthopedic & Sports Medicine; the "Rooke Vascular System"; the "Foot Waffle" available from EHOB Inc. of Indianapolis, Ind.; the "Heeler" available from BioMedical Systems; the "Cradle-Lite" available from Bird and Cronin Inc.; the Posey "Heel Protector" and "Foot Guard"; the "L'Nard Multi-Podus Orthosis System" available from L'Nard Restorative Concepts Inc. of Clearwater, Fla.; the "California Ankle Foot Orthosis—C.A.F.O." available from Capra Resources; the "E-Z Boot" foot splint available from Medassist-Op Inc. of Palm Harbor, Fla.; the "Pressure Relief Ankle Foot Orthosis" available from Anatomical Concepts, Inc. of Boardman, Ohio; and the "Pillo-Boot" Lower Leg Positioning Device available from BioPlasty Inc. of St. Paul, Minn.

Other similar devices have been disclosed in the prior art, including U.S. Pat. No. 4,478,214 which was issued Oct. 23, 1984 to William D. Lamont for "Medical Boot Apparatus and Methods of Constructing and Utilizing Same"; U.S. Pat. No. 4,197,845 which was issued Apr. 15, 1980 to Edward G. Browning for "Device for Prevention of Decubitus Ulcers on the Human Heel"; U.S. Pat. No. RE 3390 which was re-issued Oct. 17, 1989 to Ramon Berguer for "Isothermic Protective Boot"; U.S. Pat. No. 2,911,657 which was issued Nov. 10, 1959 to George W. Streeter III for "Leg and Foot Rest"; U.S. Pat. No. 3,511,233 which was issued May 12, 1970 to Elbert Holy Jr. for "Foot Protector"; U.S. Pat. No. 4,076,022 which was issued Feb. 28, 1978 to James Walker for "Therapeutic Foot and Leg Protector"; U.S. Pat. No. 3,606,884 which was issued Sep. 21, 1971 to Mary A. Peter for "Foot-Boot Apparatus"; and U.S. Pat. No. 4,813,162 which was issued Mar. 21, 1989 to Evelyn D. Gliege and Edward A. Martin for "Device for Receiving an Orthotic Insert".

SUMMARY OF THE INVENTION

The broad purpose of the present invention is to provide a medical boot which may be used either alone or together with an adjustable orthotic splint.

The boot is substantially similar to that described in my co-pending application. In my prior boot, I employed a pair of straps for closing the boot over the patients foot. The straps used mating patches of hook and loop fabric fastener materials such as Velcro fabric fasteners. However, I found that employing a boot with an outer covering having a continuous surface of small unbroken loops obviates the necessity for patches of loop-shaped fabric fastener. Such covering may comprise a brushed tricot material available from Dela, Inc., 175 Ward Hill Ave., Ward Hill, Mass. Thus, the straps require only a patch of the hook-shaped fabric fastener which may be attached to either the outer or the inner boot covering which increases the straps adjustability and accommodates the particular shape of the patient's foot and ankle.

As in my prior boot, the boot has no external binding at the seams around the sole. This structure eliminates the possibility that the boot may damage the patient's companion uncovered foot.

A separate cushion comprising a generally, rectangular, compressible body about $4'' \times 4\frac{1}{2}''$, with a pair of foldable wings, is also employed. Hook fastener patches permit the cushion to be mounted in a variety of supporting positions either inside or outside the boot.

The cushion body and the wings each have an internal sac filled with air/water/gel combination as the weight-bearing material. The cushion can be used in multiple positions within the interior or the exterior of the boot structure. It is particularly useful because it can be adjusted to custom fit the patient's heel and foot area. It can be placed beneath the leg to form a well in the boot that removes pressure from under the heel. The wings protect the lateral and medial malleolus (bony ankle prominences), cushioning and thereby reducing pressure in these areas.

For the recumbent patient, the cushion can be used in the ankle area of the boot for cushioning along the plantar surface of the foot, relieving unwanted pressure, forming a well at the bottom of the heel, or taking pressure away from the toes or the metatarsal area. The wings of the cushion relieve pressure from the side surfaces of a patient lying on lateral or medial aspects.

The cushion uses a flexible plastic container containing a gel mixed with air and water. The gel mixture provides a soft weight bearing article having special properties for retaining heat or cold. Used alone, the container can be heated in a microwave oven or warm water. It retains such heat for an extended period of time. Similarly, when cooled in a refrigerator, it remains cool for a long period of time. These properties can be used in many applications for therapeutic devices used for stimulating circulation in a patient's limb.

The boot has a leg strap with a fabric hook fastener patch sewn at one end which permits that end to be connected to the boot at an adjusted position around the calf area, thereby providing a secure fit of the leg extremities. The strap accommodates any size leg, such as a patient with a thin leg or a leg enlarged with edema.

The boot has a foot strap with a hook fastener sewn at one end which allows the fabric hooks to bite into the boot covering. The foot strap can be mounted across the in-step area of the foot portion of the boot to allow for adequate space for foot dressings and ventilation. The foot strap can also be pulled across the foot at a greater degree which reduces the open toe design thereby minimizing heat loss or promoting reflex vasodilatation which is especially important to a diabetic patient. The foot strap can be folded back for visual inspection of the patients foot for pulse checks or skin color inspection or it can be used in the open position for a foot cradle. It also dissipates excessive heat and perspiration.

The heel of the boot has a 2" slot which increases ventilation into the patients heel area, and permits examination of the heel.

A removable $3\frac{1}{4}''$ soft foam insole or liner having brushed tricot laminated on both sides covers the floor seam of the main body of the boot. The soft insole can be quickly released and turned over to use the clean surface on the opposite side. It can also be washed and air dried.

The boot also includes a plastic substantially rigid insole, about $\frac{1}{4}''$ thick, disposed inside the boot. The floor of the boot is connected to the hard insole by patches of fabric hooks, to securely hold the hard insole in position. The hard insole can be separated from the body of the boot as well as from the soft insole to launder the boot and the soft insole.

A flexible white styrene insole, about 0.100" thick is used when the $\frac{1}{4}''$ rigid insole is not used.

The bottom of the boot has a rubberized laminated sole. This external sole provides sure footing for the patient on slippery floor surfaces.

An adjustable orthotic splint positively supports the patient with correctable foot drop, with or without neuromotor deficit. In addition, the splint, combined with the boot, addresses conditions associated with foot and leg contractures, pressure ulcers and skin necrosis of the heel, leg and foot. The splint satisfies patient compliance for comfort, safety and effectiveness while offering the caregiver a complete system that requires no screw driver, screws or other such fasteners, thereby making the splint easy to use.

The splint includes a splint bar, about 11" long, which is supported on the outside of the boot, back of the ankle. A pair of fabric hook patches connect the splint bar to the boot. The lower end of the bar has a pair of spaced lugs with a group of pin-receiving openings. A right-angle hinge member has one end mounted between the lugs at an adjusted angle. The arm at the opposite end of the hinge member is then disposed at an adjusted angle with respect to the splint bar. The arm has a tongue structure that can be inserted in the slot in the heel of the boot into a complementary groove structure on the heel end of the hard insole.

The hard insole can thus be adjusted in any of three positions by a positioning pin to create either a normal position in which the patient's foot is at right angles to the patient's ankle, a second position in which the hard insole and the foot are dropped 30° from their upright position, or in a third position in which the hard insole is supported toward the user 10° from the vertical position, when the user is lying on his back. These positive settings can be achieved quickly and simply which is useful for the recumbent patient with a flaccid syndrome (foot drop). The splint is useful for conveniently varying the foot angle at prescribed intervals to change the attitude of the foot and leg muscles to avoid or correct contractures.

A stabilizing bar, mounted on the mid-section of the splint bar, can be swivelled between a position in which it is parallel to the splint bar, or a stabilizing position in which it is at right angles to the user's leg to support the foot. The stabilizing bar thus controls the rotation/anti-rotation, inversion/eversion of the hip, leg and foot.

A locking bridge is used to connect the stabilizing bars of a pair of splints for bilateral abduction or adduction to correct rotation and proper alignment of both the patient's legs.

Still further objects and advantages of the invention will be readily apparent to those skilled in the art to which the invention pertains upon reference to the following detailed description.

DESCRIPTION OF THE DRAWINGS

The description refers to the accompanying drawings in which like reference characters refer to like parts throughout the several views, and in which:

FIG. 4 is a view of a typical air/water/gel sac received in the three parts of the cushion.

FIG. 5 is a side view of the sac of FIG. 4.

FIG. 6 is a view of a preferred cuff in the laid out position.

FIG. 7 shows a cuff in the closed position.

DESCRIPTION OF THE PREFERRED EMBODIMENT

Figure 1:
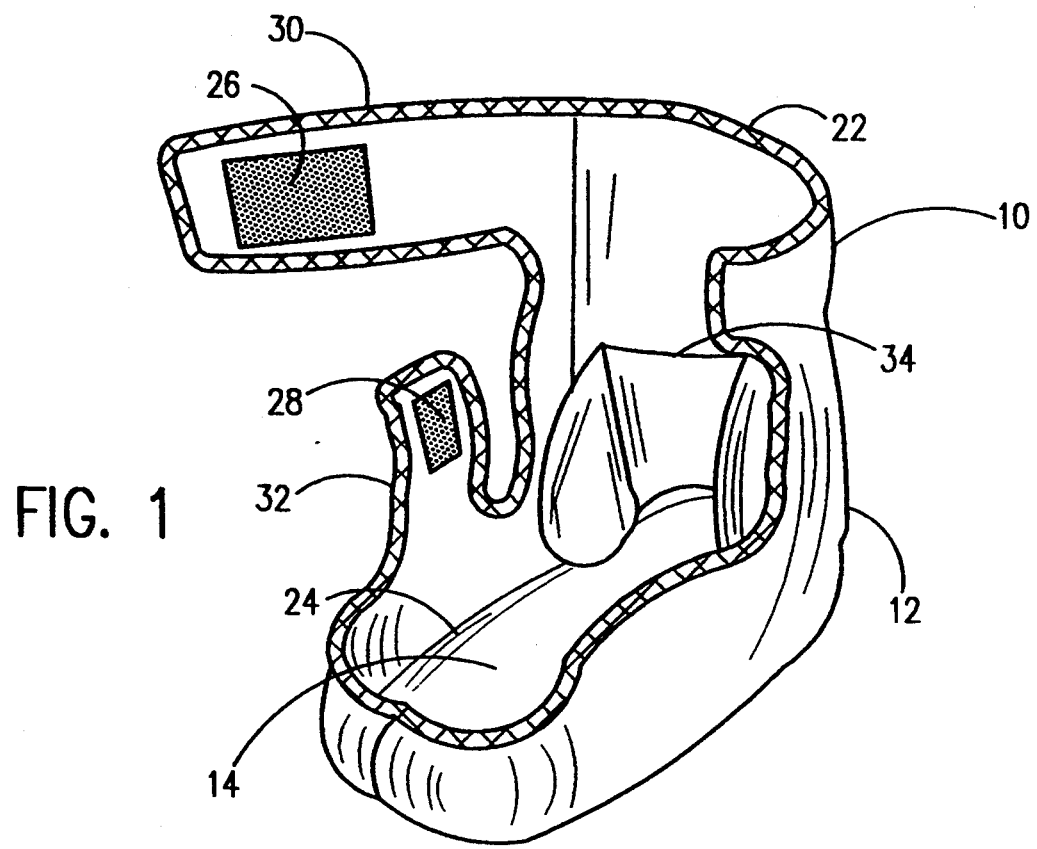
FIG. 1 is a view of a preferred medical boot illustrated in the open position.
Figure 17:
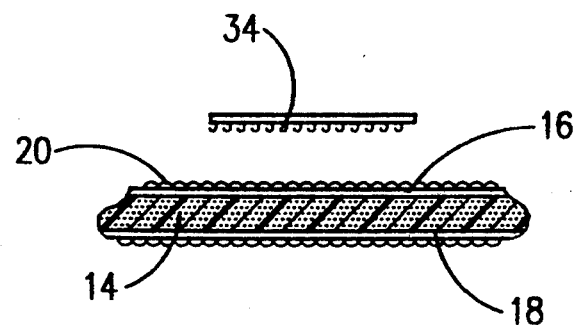
FIG. 17 shows a typical cross-section of the boot material.

Referring to FIGS. 1 end 2, a preferred medical boot 10 comprises an upper portion 12 and a bottom sole 14. The general configuration of the boot is described in my co-pending application and is formed from a multi-layer sheet containing the profile of the upper portion and the sole from which both are cut. Referring to FIG. 17, both the upper boot portion and the sole are formed of an elastomeric, shape-retaining material, such as a soft, flexible, compressible, open-core polyurethane foam 14, and inner end outer layers 16 and 18 of an ultra-smooth, soft, non-allergenic cloth such as brushed tricot. This type of cloth is characterized by a continuous layer of small loops 20 which makes the material compatible with fabric hook fastener means such as Velcro fasteners. The entire Inner and outer covers of both the upper portion of the boot end the sole have a brushed tricot covering so that a patch of a Velcro-type hook material can be connected in any position on the boot.

An over edge binding 22 is stitched around the entire edge of the upper portion of the boot to strengthen the perimeter against fraying as well as to provide a seam. A similar over edge binding 24 is stitched around the inside seam between the sole and the upper portion of the boot. The boot is initially sewn together inside out and then turned right side out to place the bindings on the inside so that they will not rub against the patients other foot.

Figure 2:
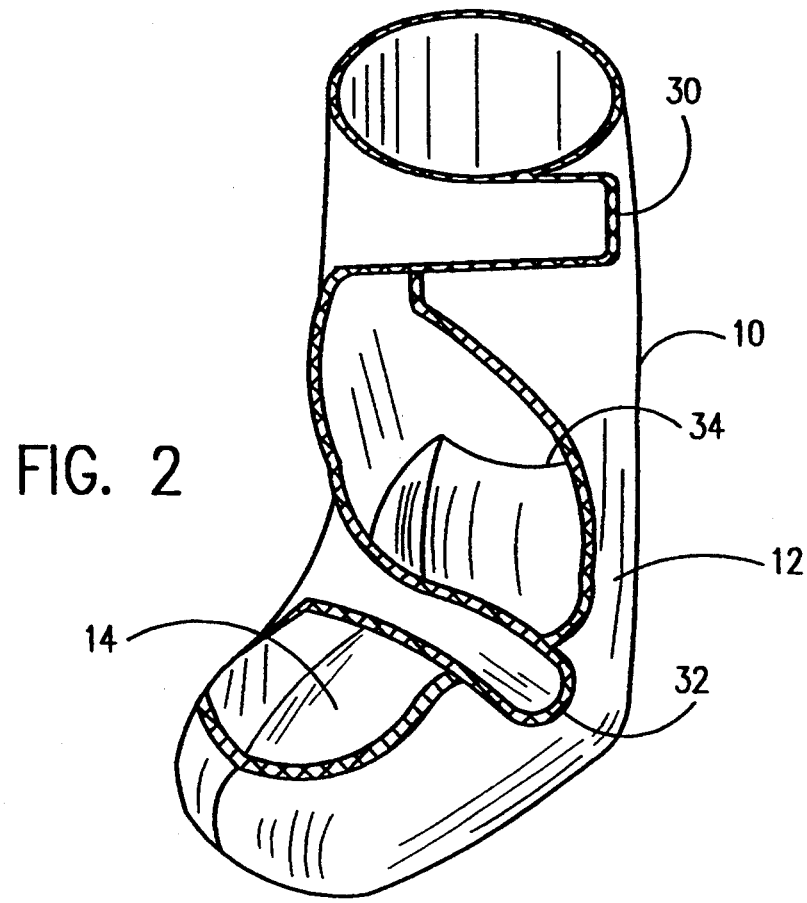
FIG. 2 shows the boot in the closed position.

The boot has two patches 26 and 28 of a hook-shaped fabric fastener near the outer end of an ankle strap 30 and the outer end of foot strap 32, respectively. The fabric hook fastener material may be a Velcro fabric fastener and is characterized by a plurality of small fabric hooks 34, as can be seen in FIG. 17. Thus both boot straps with the patches of fastener material can be connected to the opposite side of the boot opening, as illustrated in FIG. 2 in any selected position. The location of the connection is not limited to the position of a matching patch.

Figure 3:
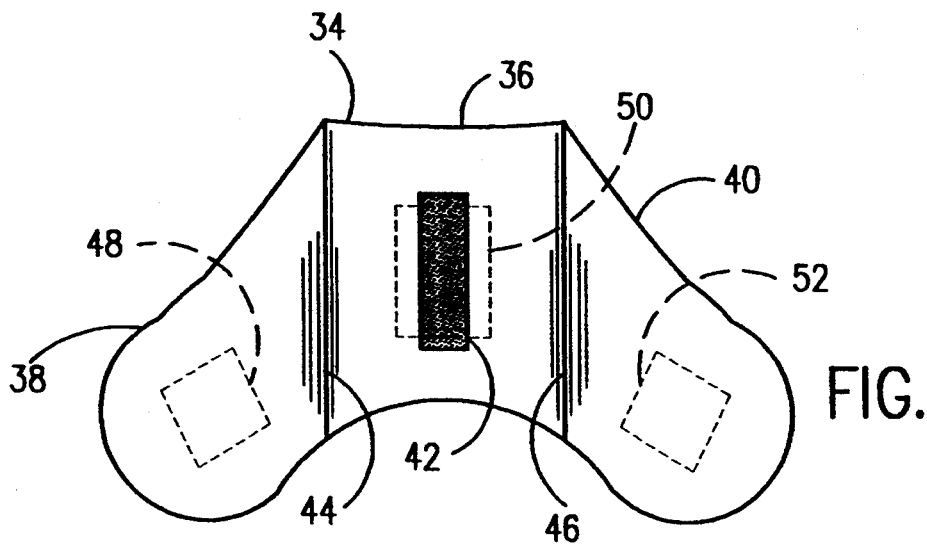
FIG. 3 illustrates the foldable cushion.

The boot also employs a cushion 34, illustrated in FIG. 3, which is very similar in configuration to the cushion illustrated in my co-pending application. Cushion 34 has a central portion 36 and a pair of side panels or wings 38 and 40. It is similar in construction to the boot, formed with an inner core of a flexible, compressible open core polyurethane foam with an outside covering of a brushed tricot material, that is, a material having a continuous surface of closed loops. A patch 42 of a Velcro fabric hook-type fastener material is attached to one side of central portion 36. Central portion 36 has a somewhat rectangular configuration while side panels 38 and 40 extend at about a 45° angle from foldable parallel fold lines 44 and 46 with respect to the central body portion.

The central body portion and the two side panels each have an internal recess for receiving flexible plastic sacs 48, 50, and 52 respectively. A typical sac 50 is illustrated in FIGS. 4 and 5 and comprises a flexible, sealed, fluid-tight plastic container 52 about 3¾"×5". FIG. 5 shows the typical container partially broken away to show the internal air/water/gel material 54 which fills the plastic container. The gel is material mixed with a combination of bubbles of air, water and the gel. The mixture gives a cushioning effect and also can be used to either warm or cool a patient's limb because of its ability to retain either heat or a low temperature for a long period of time. When used separately from the cushion, the sac can be heated either in a microwave oven or in warm water. Alternatively, it can be cooled in a refrigerator. I believe the bubbles of air and water in the gel change the heat retaining properties of the gel. The gel mixture is available from Cold Ice, Inc., Oakland, Calif.

Sac 50 is illustrative of the sacs in the three portions of the cushion. Similar sacs may be employed in other parts of the boot. The sac is very compressible and soft and at the same time provides support for a user's limb placed on that portion of the cushion containing the sac.

Figure 18:
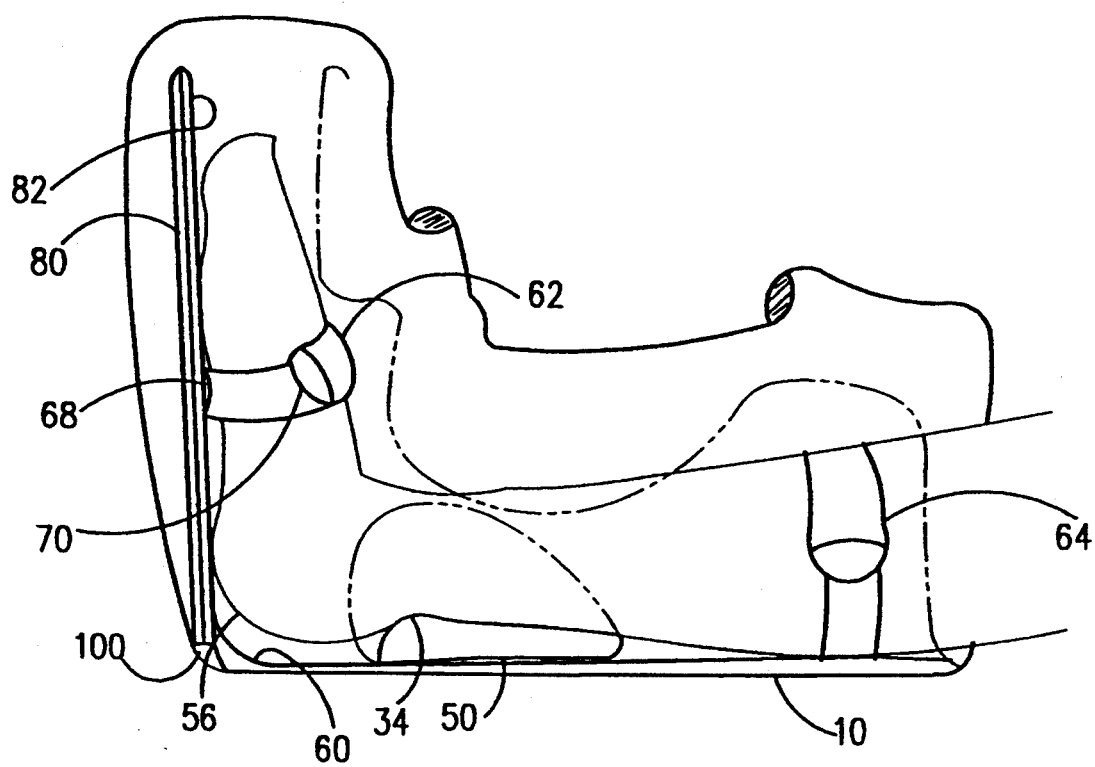
FIG. 18 is a view of a user's foot super-imposed over the outline of a boot, showing the relationship between the foot and ankle supported by the two cuffs and the cushion.

Cushion 34 can be readily connected to either the inside or the outside of the boot in any selected position. FIG. 18 illustrates the manner in which the user's foot 56 may be disposed on the cushion. The cushion can be adjusted according to the configuration of the user's ankle and leg so as to support the leg while providing a well 60 beneath the user's heel. Fastener patch 42 then maintains the cushion in the selected distance from the heel of the boot.

A pair of cuffs 62 and 64 are wrapped around the foot portion and the leg portion respectively of the user's leg. The two cuffs are similar in construction, each comprising the same type of inner material and outer covering as the boot. Cuff 62 is illustrated in FIGS. 6 and 7. For illustrative purposes, the cuff is 13" long, 3" wide and has two patches 66 and 68 of a fabric hook type fastener. The two patches are preferably about 1¼" in diameter. Patch 66 is located about ½" from the one end of the cuff; the other patch 68 is located about 4" from the edge of patch 66. The arrangement is such that when one end 70 is coiled adjacent the opposite end 72, patch 66 forms a releasable attachment to the cover material adjacent end 70, as illustrated in FIG. 7. The other patch 68 is then on the outside of the cuff.

Cuff 62 has an internal recess with a sac 74 of a mixture of air, water and gel that is identical to sac 50. Sac 74 is located in a fixed position in the cuff and provides a soft cushion, as illustrated in FIG. 18, when the cuff is wrapped around the user's foot and locked into position by fastener patch 68 in a manner that will presently be described. The sac has a sufficient thickness to separate the sole of the user's foot from the bottom of the boot, thus avoiding any abrasions or pressures sores between the user's foot and the boot material.

Cuff 64 is identical to cuff 62 except that it does not have a sac of the gel material. The cuff 64 is also connected by a fabric fastener patch to the inside covering of the boot so that the relationship between the boot heel and the cuff is maintained in a fixed position.

A second thin cuff 64 can be wrapped around the user's foot when the cushioned cuff 62 is not being used.

Figure 22:
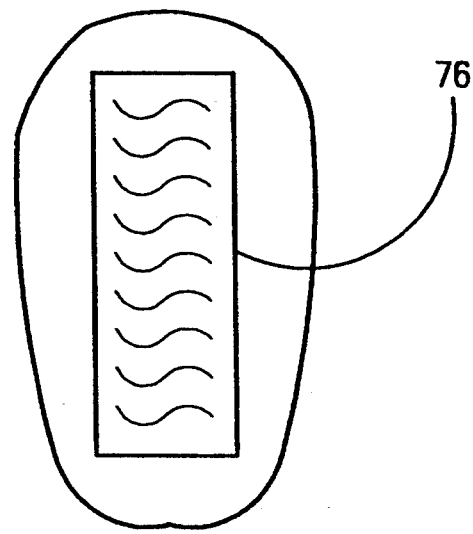
FIG. 22 is a view of the bottom of the boot sole.

Referring to FIG. 22, a rubberized sole 76 is attached to the bottom outside sole of the boot to provide sufficient friction so that the user can walk with the boot on a smooth surface.

Figure 8:
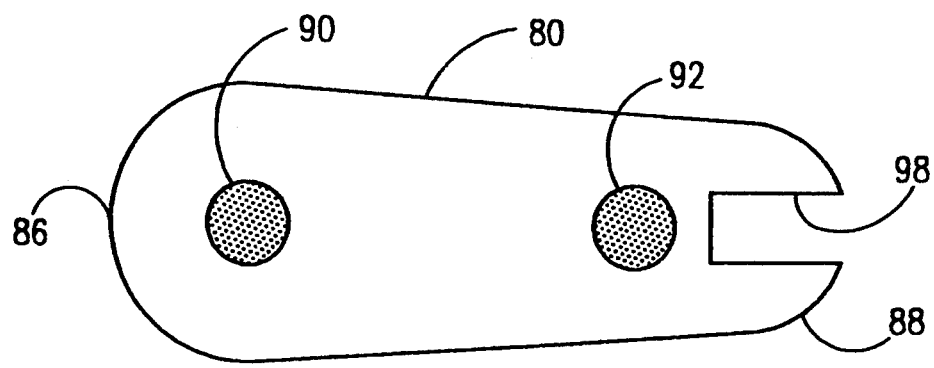
FIG. 8 is a plan view of the hard insole.
Figure 9:
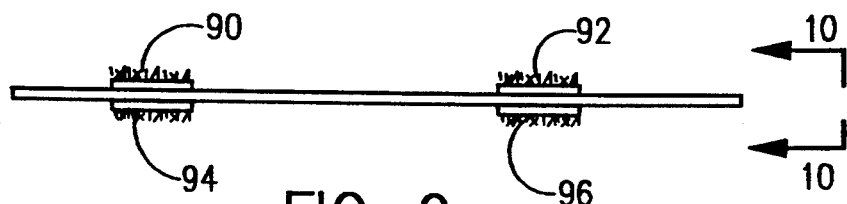
FIG. 9 is an edge view of the hard insole.
Figure 11:
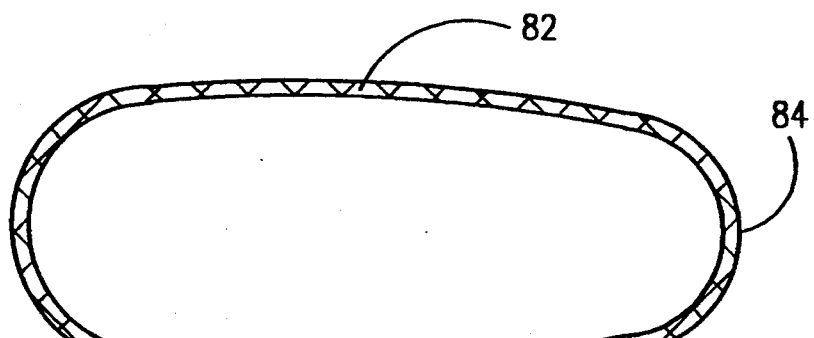
FIG. 11 is a plan view of the soft insole.
Figure 12:
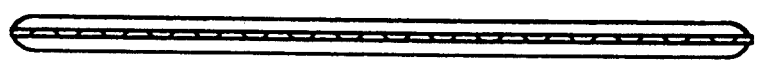
FIG. 12 is a side view of the soft insole.

A pair of insoles 80 and 82, illustrated in FIGS. 8 and 11 respectively, may be used in the boot. Insole 82 is soft, having an edge configuration slightly smaller than the bottom inside of the boot so that it can be inserted in the boot to protect the bottom of the user's foot. Insole 82 is made with the same construction as the boot, that is with a compressible inner liner, a brushed tricot covering, and a $\frac{3}{4}''$ stitched binding 84 around its perimeter.

Hard insole 80 is formed of a relatively rigid polypropylene plastic material with an outside contour slightly smaller than soft insole 82 and a $\frac{1}{4}''$ thickness. Insole 80 is intended to be inserted in the bottom of the boot and connected to the bottom of the soft insole.

Hard insole 80 has a toe end 86 and a heel end 88. Two patches of hook fabric fasteners 90 and 92 are attached to one side of the hard insole about 6" apart, along the center line of the insole. Each patch is about $1\frac{1}{4}''$ in diameter.

A second pair of fabric fastener patches 94 and 96 are mounted on the opposite side of the hard insole in the same relative position as patches 90 and 92. Thus when the hard insole is placed in the bottom of the boot, lower patches 94 and 96 engage the fabric loops on the covering of the bottom of the boot to releasably lock the hard insole in position.

Similarly when the soft insole is mounted on top of the hard insole, patches 90 and 92 releasably lock the soft insole in position. The assembly can be readily removed from the boot for cleaning the insoles as well as the boot.

Figure 10:
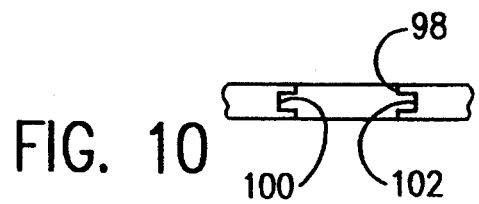
FIG. 10 is a view as seen along lines 10—10 of FIG. 9.

Referring to FIGS. 8 and 10, the heel end of the hard insole has a slot 98, 1" wide and $2\frac{3}{8}''$ deep. The side edges of the slot have opposed longitudinal grooves 100 and 102.

FIG. 18 shows the relative position of the hard insole with respect to the body of the boot. The boot also has a $1\frac{1}{2}''$ horizontal stitched opening 100 along the seam between the upper portion of the sole of the boot. Opening 100 provides access to slot 98 of the hard insole as well as permitting a visual inspection of the user's heel without removing the boot.

Figure 13:
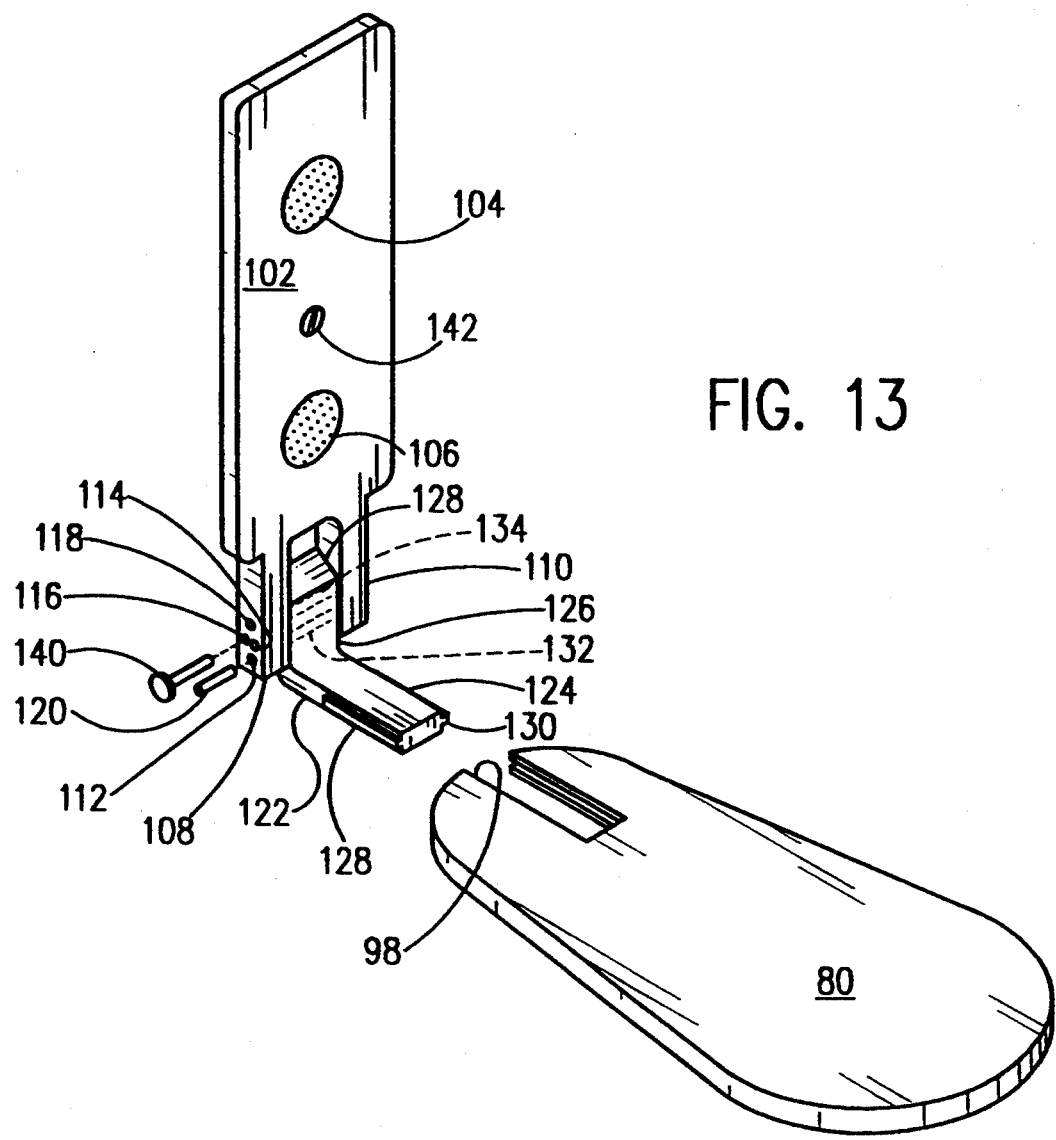
FIG. 13 is a partially exploded view of the adjustable splint and its relationship to the hard insole.

FIG. 13 illustrates splint bar 102 and its relationship to hard insole 80. Splint bar 102 is also formed of a rigid polypropylene material, 3" wide, 9" long, and $\frac{1}{4}''$ thick. The inside face of the splint bar has a pair of $1\frac{1}{4}''$ diameter hook fabric fastener patches 104 and 106 located about 3" apart. Patches 104 and 106 provide means for connecting the splint bar to the outside back surface of the boot. Patches 104 and 106 can be readily attached to any suitable location on the boot cover.

Splint bar 102 has a pair of parallel lugs 108 and 110 which are $2\frac{1}{2}''$ long and spaced $1\frac{3}{8}''$ apart. The two lugs have four pairs of aligned openings 112, 114, 116 and 118. A hinge pin 120 is slideably received in aligned hinge openings 112 with a slight friction fit so that it remains in the opening unless pushed out.

An angular hinge member 122 connects the splint bar to the hard insole. Hinge member 122 has a leg 124, and a second leg 126 disposed at right angles to leg 124. Leg 124 has about a $3\frac{3}{4}''$ length permitting it to be inserted in heel opening 100 of the boot. The opposite side edges of leg 124 have longitudinal tongues 128 and 130 which are slideably received in grooves 100 and 102 of the heel end of the hard insole, forming a tongue and groove connection between the hinge member and the hard insole. The tongues are frictionally retained in the grooves so that it takes some effort to pull the hinge member from the hard insole heel opening.

Short leg 126 has about a 2" overall length including a tapered toe 128. Leg 126 has a pair of spaced parallel transverse openings 132 and 134.

When the short leg of the hinge member is inserted between the two lugs of the splint bar, opening 132 is aligned with openings 112 in the lugs. Hinge pin 120 is then inserted through the openings in the lugs and the hinge member so that the hinge member is pivotable with respect to the splint bar. The other opening 126 can then be aligned with either openings 114 or 116 by swinging the hinge member.

Figure 19:
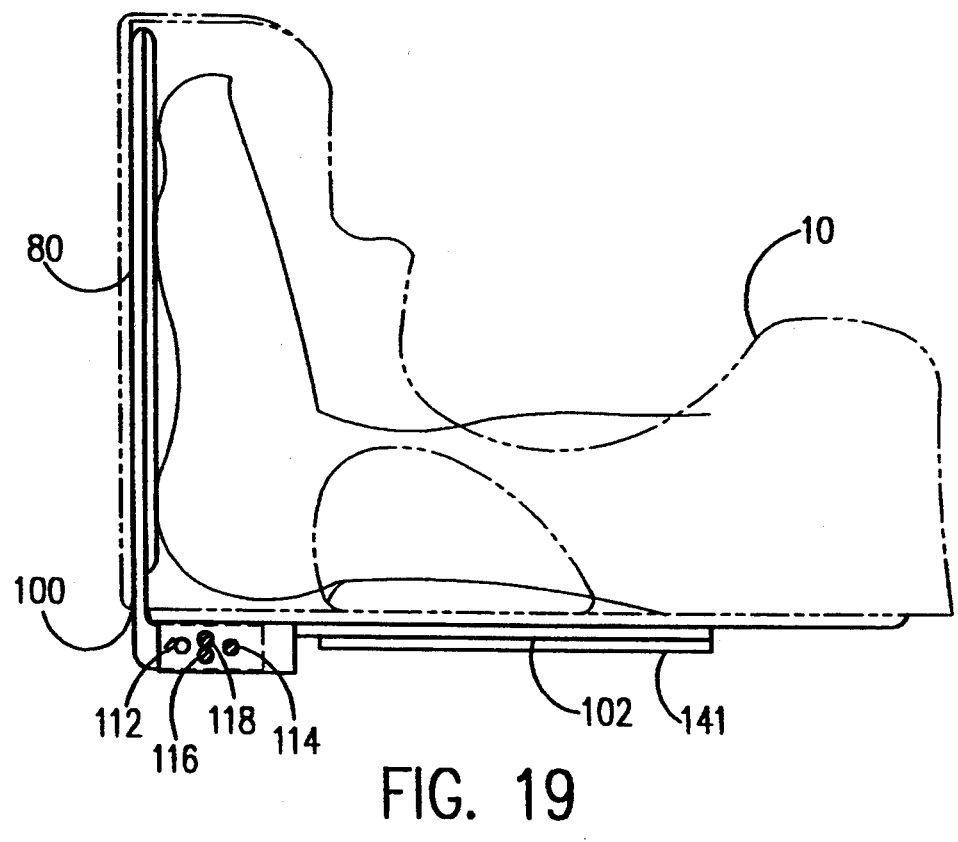
FIG. 19 is a view showing the manner in which the splint bar and the hard insole support the foot in the normal foot position.

Referring to FIGS. 13 and 19, when opening 126 is aligned with openings 116, a locking pin 140 is inserted in the aligned openings to connect the hinge member and the lugs in such a manner that the hard insole is disposed at a 90° angle with respect to the plane of the splint bar.

Figure 20:
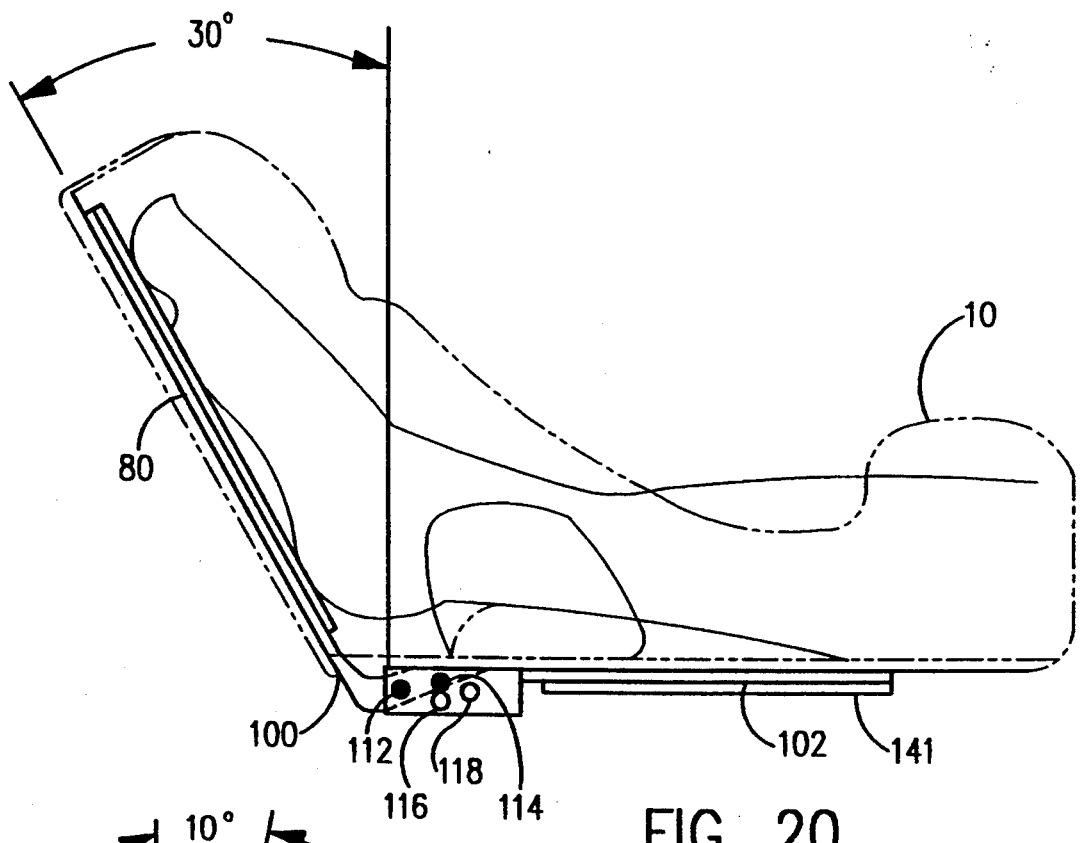
FIG. 20 is a view showing how the splint bar and the hard insole cooperate to support the foot in an extension position of about 30° from the vertical.

Referring to FIG. 20, if the hard insole is swung to align opening 126 with openings 114 in the lugs, locking pin 140 can be inserted in openings 114 and 126 to lock the hard insole in a position 30° from the normal vertical foot position so that the foot has an extension of 30°.

Figure 21:
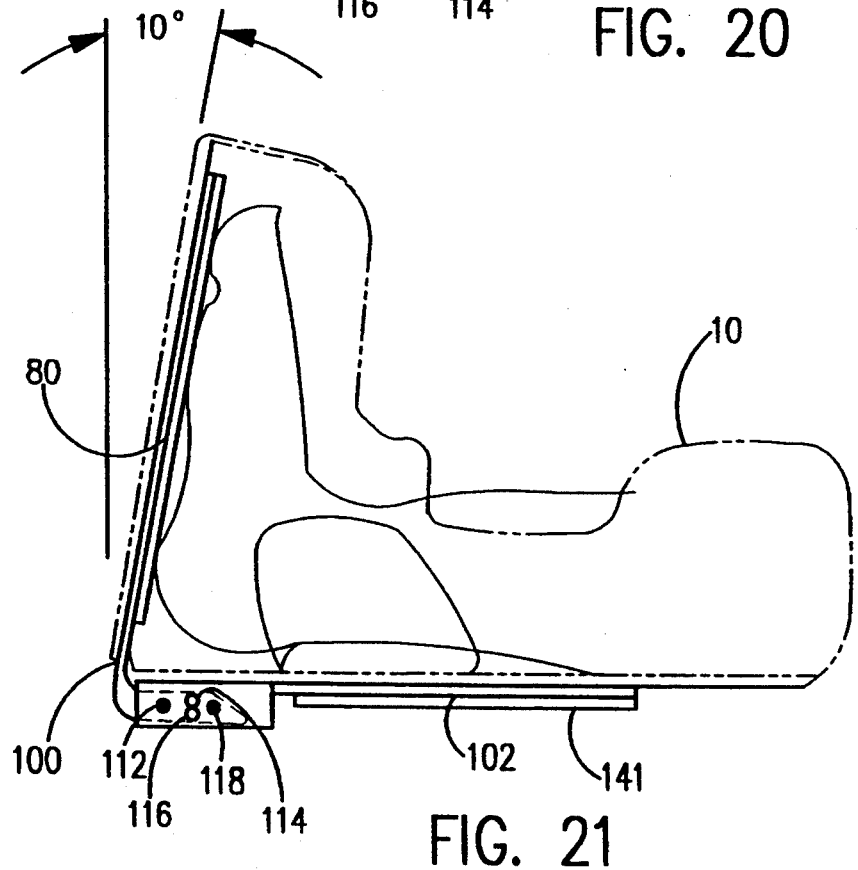
FIG. 21 is a view showing how the splint bar end the hard insole cooperate to support the foot in the flexion position of about plus 10°.

Referring to FIG. 21, if the hinge member is pivoted toward the splint bar, to position toe 128 beneath opening 114 as illustrated in FIG. 21, the locking pin is inserted in openings 118, the hard insole will be disposed in a flexion position, that is about 10° from the right angle position. The user's foot prevents the hard insole from moving clockwise toward the 90° position, while the locking pin prevents the hard insole from moving counterclockwise toward the 90° position, as viewed in FIG. 21.

Figure 14:
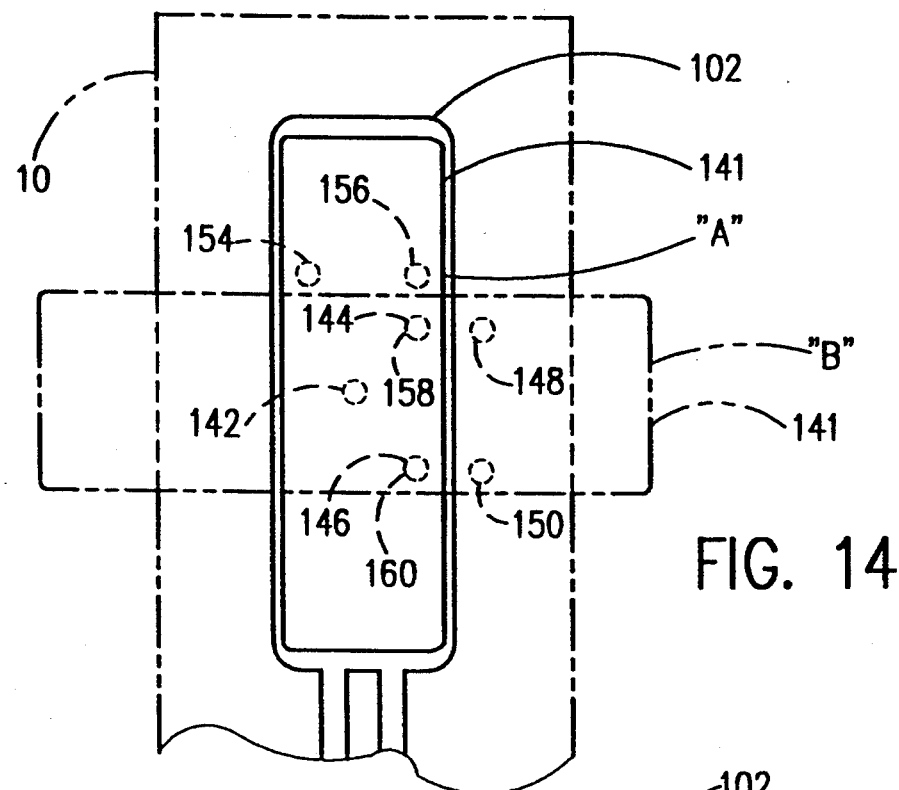
FIG. 14 is a view of the splint bar and the stabilizer bar, and showing the stabilizer bar in its stabilizing position in phantom.
Figure 15:
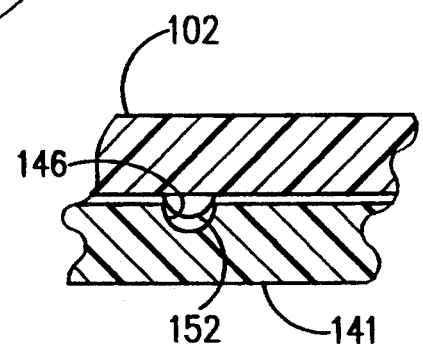
FIG. 15 is a fragmentary, sectional view of a typical locking knob for the stabilizer bar.
Figure 16:
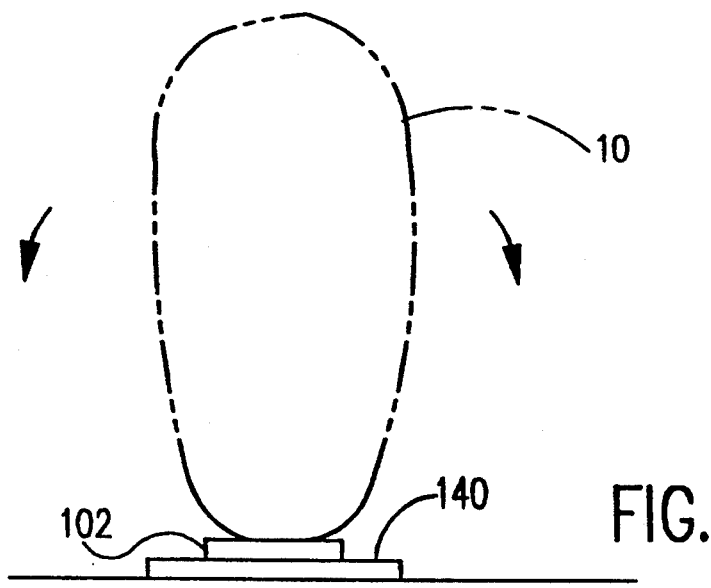
FIG. 16 is a view illustrating the manner in which the stabilizing bar prevents the boot from rolling over from its upright position.

Referring to FIGS. 14 to 16, a stabilizer bar 141 is connected to the splint bar. The stabilizer bar has essentially the same width as the splint bar, is slightly shorter than the splint bar and is $\frac{1}{4}''$ thick. The splint bar and the stabilizer bar are shown in a face-to-face relationship. Pin means 142 connect the stabilizer bar to the splint bar so that the stabilizer bar can be moved from a parallel position illustrated at "A" to an outer position illustrated at "B" in which it is at right angles to the splint bar and the user's leg. Both the stabilizer bar and the splint bar have a width substantially less than the width of boot 10.

The stabilizer bar has four recesses 144, 146, 148 and 150. A typical recess 148 is illustrated in FIG. 15. A rounded nub 152 is also illustrated in FIG. 15. A nub is located at positions designated at 154, 156, 158 and 160. The recesses and nubs are located on the splint bar and the stabilizer bar so as to releasably lock them in either position "A" or in position "B".

Referring to FIG. 16, when stabilizer bar is in its outer position, it extends beyond the side profile of the boot in such a manner that when the patient is lying in a supine position, the stabilizer bar through its connection with the splint bar and the hard insole prevents the user's foot from rotating in either the right or the left in the direction of the arrows illustrated in FIG. 60. The stabilizer bar prevents the boot from swinging about the side edges of the splint bar.

Figure 24:
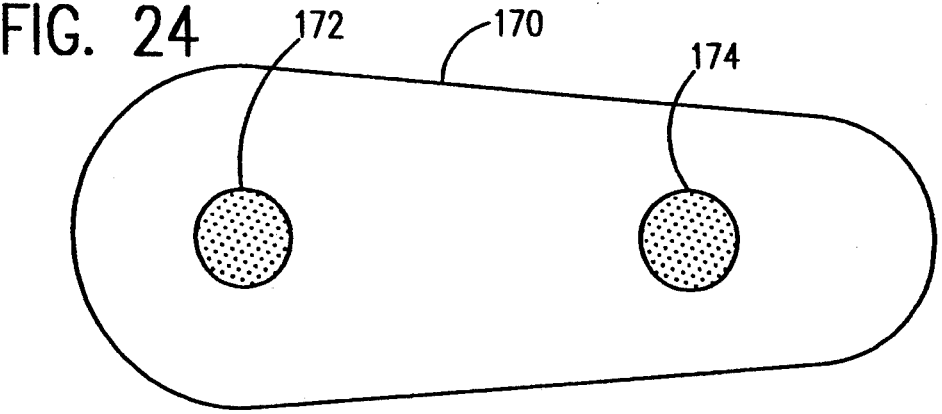
FIG. 24 illustrates a flexible plastic insole used when the hard insole is not being used.

Referring to FIG. 24, a flexible, semi-rigid insole 170 having generally the same configuration as hard insole 80, but without slot 98, is used when the patient does not use either the splint on the hard insole. Insole 170 is about 0.100" thick and formed of a white styrene plastic. It has hook fabric fastener means 172 and 174 on both of its sides for connection to the boot bottom and the soft insole.

Figure 23:
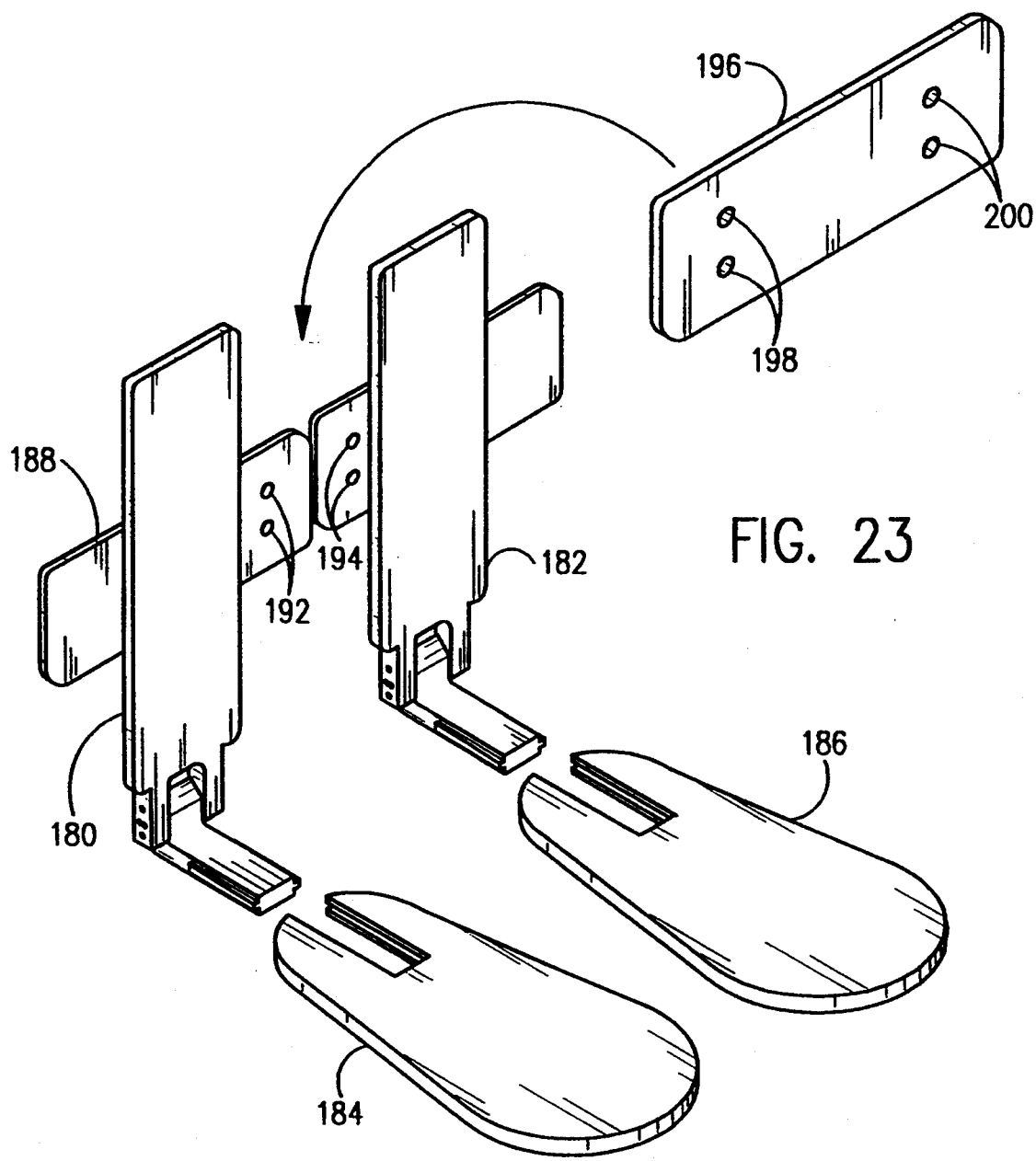
FIG. 23 Is an exploded view showing how two splints are connected by a bridge member.

Referring to FIG. 23, a pair of splint bars 180 and 182, identical to splint bar 102 may be used for both feet of a patient. The two splint bars are adapted to be connected to a pair of hard insoles 184 and 186, respectively. The hard insoles are identical to hard insole 80.

The two splint bars support a pair of stabilizer bars 188 and 190, respectively. A rigid bridge bar 196, having the same width and thickness as the stabilizer bars may be connected to the stabilizer bars, in their open positions illustrated in FIG. 23. Nubs 198 mate with recesses 192, and nubs 200 mate with recesses 194 to releasibly lock the stabilizer bars in their open position. The bridge bar prevents the two stabilizer bars from from swinging toward one another, and cooperate in keeping the user's feet, connected to the hard insoles by the preferred boot, from moving toward one another. The integrated structure locks the patient's feet together in a supported position.

Thus it is to be understood that i have described an improved medical boot that can be used to support the user's foot in multiple positions as well as preventing foot-drop and pressure sores. The improved medical boot employs a cushion that can also be used in multiple positions within either the interior or the exterior of the boot structure. It readily adjusts to custom fit the patient's heel and foot area to the boot, and can be placed in the boot near the heel to form a well removing pressure from the back of the heel. The wings of the cushion protect the bony ankle prominences thereby greatly reducing pressure areas. The boot can be used for either a recumbent or an ambulatory patient. For the recumbent patient, the strap with the cushioned sac can be used for cushioning at an adjusted position along the plantar surface of the foot, relieving unwanted pressure, and forming a well at the bottom of the heel for removing pressure away from the toes or the metatarsal area. For the patient lying on the lateral or medial aspects, the wings of the cushion take pressure away from the sides of the user's limb. One or several air/water/gel sacs can be used and adjusted in various positions in the interior of the boot structure.

The boot and the cushion can be used in conjunction with a splint at the plantar surfaces of the user's leg to increase or reduce friction. Employing the boot covering with a continuous loop construction provides means for connecting straps 30 and 32 in any suitable position around the calf area thereby providing a secure fit of the leg extremity. The straps accommodate any leg size, either a thin leg or a leg enlarged with edema. Further, the straps because of their adjustability, provide room for adequate foot dressings and ventilation. They can be pulled across at a greater degree to reduce the open-toed design thereby minimizing heat loss. The straps can be folded onto the back of the boot for convenient visual inspection for a pulse check, and skin color inspection or the boot can be used in the open position as a foot cradle. The straps can be opened to permit the boot to dissipate excessive perspiration.

The preferred cuffs provide greater cushioning for all pressure points of the lower extremity.

The slot at the base of the heel is a surged slot, allowing for greater ventilation of the heel, permitting examination of the heel placement and allowing for connection of the splint.

The soft insole covers the entire floor seam of the main body of the boot. It can be washed and air dried. It is attached to the hard insole by the fabric fastener patches.

The hard insole also has a large exposed plastic surface with the patches fastened to the plastic by a high temperature adhesive. The patches also function to secure the soft insole in a position so that it can be separated from the body of the boot for laundering the boot and/or insole can be laundered.

The internal cuffs can be adjusted to a comfortable position while securing the leg to the inside structure of the boot. The ankle cuff can be adjusted up or down along the inside wall of the boot, avoiding abrasion of any existing wound or ulcer which may be present on the leg. The foot cuff keeps the foot in proper alignment in the boot. In the recumbent or ambulatory position, the foot cuff with a sac of air/water/gel acts as a cushioning device and relieves pressure from the metatarsal and toe area. The foot cuff can be adjusted to a comfortable position according to the configuration of the patient's foot, and can be moved down along the plantar surface of the foot avoiding irritating any existing wounds or ulcer conditions.

The splint is a multi-functional orthosis providing a positive setting for a patient with a correctable foot drop, or without neuromotor deficit. In addition, the splint, in conjunction with the boot, addresses conditions associated with foot and leg contractures, pressure ulcers and skin necrosis of the heel, leg and foot, and satisfies patient compliance for comfort, safety and effectiveness. The positive settings of the hard sole with a splint bar are achieved simply and quickly at the hinge by aligning the holes to the desired angle and inserting the locking pin. The splint bar can be easily removed from the patient. Further, it can be adjusted to vary the foot angle at prescribed intervals to change the attitude of the foot and leg muscles to correct contractures.

The stabilizing bar stabilizes the integrated rigid insole, thus controlling rotation or anti-rotation, inversion-eversion of the hip, leg and foot. A locking bridge can also be used with two splints for bi-lateral abduction or adduction.

Having described my invention, I claim:

1. A medical boot, comprising:
   a substantially boot-shaped main body portion formed primarily of a substantially soft, flexible, compressible, shape-retaining material having a foot portion, an ankle portion; and a heel opening;

splint means for supporting the limb of a user with his foot disposed in the boot-shaped main body portion comprising:

a substantially rigid insole connected to the foot portion of the main body portion of the boot so as to moveable therewith;

the insole being disposed in the foot portion of the boot;

a substantially rigid splint bar, and means for connecting the splint bar to the ankle portion of the boot;

hinge means for connecting the insole to the splint bar such that the insole is moveable to a selected angular position with respect to the splint bar;

the hinge means comprising an elongated hinge member having one end received in the heel opening and connected to the insole;

pin means connecting the opposite end of the hinge member to the splint bar; and means for locking the hinge means in said selected angular position, comprising the splint bar having a pair of spaced lugs, said hinge member being received between the lugs, the lugs having pairs of aligned openings, the hinge member having a toe swingeable between the pairs of aligned openings, and locking pin means being received in a selected aligned pair of said openings in the lugs to engage the toe of the hinge in a selected angular position.

2. A medical boot comprising:

a substantially boot-shaped main body portion formed primarily of a substantially soft, flexible, compressible, shape-retaining material having a foot portion and an ankle portion;

splint means for supporting the limb of a user with his foot disposed in the boot-shaped main body portion, comprising:

an elongated substantially rigid insole connected to the foot portion of the main body portion so as to be moveable therewith;

an elongated substantially rigid splint bar, and means for connecting the splint bar to the ankle portion of said main body portion;

articulated hinge means for connecting one end of the insole to one end of the splint bar, the articulated hinge means including a hinge pin disposed such that the insole is pivotal about the hinge pin to a first selected angular position with respect to the splint bar; and means for locking the hinge means in said selected angular position including a locking pin mounted on the hinge means adjacent the hinge pin, in a position depending upon the selected angle of the insole to the splint bar, the locking pin being removable from the hinge means so as to be repositioned according to a second selected angular position of the insole with respect to the splint bar.

3. A medical boot as defined in claim 2, in which the insole is pivotal to a selected angle less than 180° but greater than 90° with respect to the splint bar; and the main body portion is adapted to receive a patient's foot between the insole and the splint bar on one side of the splint bar to generally conform to said selected angle, and both the locking means and the hinge means are located on the opposite side of the splint bar or the patient's foot, whereby the locking means is not disposed in a lateral position with respect to the patient's foot.

* * * * *